US011470784B2

(12) United States Patent
Gauvreau, Jr.

(10) Patent No.: US 11,470,784 B2
(45) Date of Patent: Oct. 18, 2022

(54) UNMANNED AERIAL VEHICLE FOR AUGMENTING PLANT POLLINATION

(71) Applicant: Paul Richard Gauvreau, Jr., Rancho Santa Fe, CA (US)

(72) Inventor: Paul Richard Gauvreau, Jr., Rancho Santa Fe, CA (US)

( * ) Notice: Subject to any disclaimer, the term of this patent is extended or adjusted under 35 U.S.C. 154(b) by 594 days.

(21) Appl. No.: 16/495,818

(22) PCT Filed: Mar. 21, 2018

(86) PCT No.: PCT/US2018/023524
§ 371 (c)(1),
(2) Date: Sep. 19, 2019

(87) PCT Pub. No.: WO2018/175552
PCT Pub. Date: Sep. 27, 2018

(65) Prior Publication Data

US 2020/0022312 A1 Jan. 23, 2020

Related U.S. Application Data

(60) Provisional application No. 62/474,534, filed on Mar. 21, 2017.

(51) Int. Cl.
*A01G 2/00* (2018.01)
*B64C 39/02* (2006.01)

(52) U.S. Cl.
CPC .............. *A01G 2/00* (2018.02); *B64C 39/024* (2013.01); *B64C 2201/042* (2013.01);
(Continued)

(58) Field of Classification Search
CPC . A01H 1/027; A01G 2/00; A01G 7/00; B64C 39/024; B64C 2201/042; B64C 2201/108; B64C 2201/12; B64C 2201/141
See application file for complete search history.

(56) References Cited

U.S. PATENT DOCUMENTS 1,749,471 A * 3/1930 De Bothezat ........... B64C 27/08 244/17.23
3,053,480 A * 9/1962 Vanderlip ............. B64C 39/024 244/17.13

(Continued)

FOREIGN PATENT DOCUMENTS

CN 103503764 B 7/2015
JP 2011244750 A 12/2011

(Continued)

OTHER PUBLICATIONS

Bee Culture "Catch the buzz—creation of robot bee to pollinate crops," published online Dec. 20, 2016; available at http://www.beeculture.com/catch-buzz-creation-robot-bee-pollinate-crops/.

(Continued)

*Primary Examiner* — Medhat Badawi
(74) *Attorney, Agent, or Firm* — Morrison and Foerster LLP

(57) ABSTRACT

A method of pollinating a plant: flying an unmanned aerial vehicle above the plant and generating a thrust that contacts the plant, that produces a sound pressure level of at least $6\times10^{-5}$ Pascal at the plant, and that produces a frequency that induces the plant to release pollen.

18 Claims, 6 Drawing Sheets

102
104
104
104
104
106
108

(52) U.S. Cl.
CPC .... *B64C 2201/108* (2013.01); *B64C 2201/12* (2013.01); *B64C 2201/141* (2013.01)

(56) References Cited

U.S. PATENT DOCUMENTS

| | | | | |
|---|---|---|---|---|
| 3,286,403 | A * | 11/1966 | Tanke | A01H 1/027 47/1.41 |
| 3,463,398 | A * | 8/1969 | Smith et al. | A01C 17/001 239/675 |
| 3,688,952 | A * | 9/1972 | Barlow | B64D 1/16 222/333 |
| 9,346,546 | B2 * | 5/2016 | Markov | B64C 39/024 |
| 9,540,105 | B2 * | 1/2017 | Markov | B05C 19/008 |
| 9,589,448 | B1 * | 3/2017 | Schneider | F41H 11/00 |
| 9,807,996 | B1 * | 11/2017 | Yu | A01M 29/00 |
| 9,852,644 | B2 * | 12/2017 | Salnikov | A01C 7/04 |
| 9,977,435 | B2 * | 5/2018 | Fisher | G08G 5/0034 |
| 10,514,691 | B2 * | 12/2019 | Cantrell | G05D 1/0094 |
| 10,520,953 | B2 * | 12/2019 | Cantrell | B60L 53/51 |
| D875,023 | S * | 2/2020 | Lee | D12/328 |
| 10,599,959 | B2 * | 3/2020 | Buoro | G06V 20/188 |
| 10,814,980 | B2 * | 10/2020 | Zvara | B64D 1/16 |
| 10,822,085 | B2 * | 11/2020 | Ott | B05B 13/005 |
| 10,836,484 | B2 * | 11/2020 | Volpi | B25J 15/00 |
| 10,850,866 | B2 * | 12/2020 | Fisher | B64C 29/02 |
| 10,919,610 | B2 * | 2/2021 | Araujo | B64C 39/024 |
| 10,919,625 | B2 * | 2/2021 | Anderson | B64C 39/024 |
| 11,001,380 | B2 * | 5/2021 | Nahuel-Andrejuk | B64C 39/024 |
| 11,027,294 | B2 * | 6/2021 | Roy | B05B 3/0409 |
| 11,059,582 | B2 * | 7/2021 | Nahuel-Andrejuk | G05D 1/0094 |
| 11,066,167 | B2 * | 7/2021 | Bennett | A01B 79/02 |
| 11,130,573 | B2 * | 9/2021 | Holly | G05D 7/0617 |
| 11,194,348 | B2 * | 12/2021 | Maor | G08G 5/0073 |
| 11,235,874 | B2 * | 2/2022 | Jones | B64D 1/18 |
| 11,242,147 | B2 * | 2/2022 | Zvara | B64D 1/02 |
| 11,304,380 | B2 * | 4/2022 | Patrick | A01G 9/0291 |
| 11,319,064 | B1 * | 5/2022 | Wittmaak, Jr. | B64C 1/1415 |
| 11,337,358 | B2 * | 5/2022 | Fletcher | A01G 9/0293 |
| 11,338,921 | B2 * | 5/2022 | Holly | B05B 1/20 |
| 2013/0068892 | A1 * | 3/2013 | Bin Desa | B64C 39/024 701/4 |
| 2013/0134254 | A1 * | 5/2013 | Moore | B64D 1/16 244/17.11 |
| 2013/0305600 | A1 * | 11/2013 | Whaley | A01H 1/027 47/1.41 |
| 2014/0163781 | A1 * | 6/2014 | Vian | G01S 7/4802 701/3 |
| 2014/0246545 | A1 * | 9/2014 | Markov | B05C 19/008 244/190 |
| 2014/0249693 | A1 * | 9/2014 | Stark | B64C 39/024 701/2 |
| 2014/0303814 | A1 * | 10/2014 | Burema | A01C 21/00 901/1 |
| 2015/0023566 | A1 * | 1/2015 | Fryshman | A01M 3/00 382/110 |
| 2015/0041596 | A1 * | 2/2015 | Markov | B64D 1/16 244/190 |
| 2015/0181819 | A1 * | 7/2015 | Celebi | B64C 39/024 701/2 |
| 2016/0334276 | A1 * | 11/2016 | Pluvinage | G01J 3/28 |
| 2017/0032686 | A1 * | 2/2017 | Alonso Tabares | G08G 5/0091 |
| 2017/0231213 | A1 * | 8/2017 | Gordon | A01M 25/00 43/132.1 |
| 2018/0065749 | A1 * | 3/2018 | Cantrell | G06V 20/17 |
| 2018/0072414 | A1 * | 3/2018 | Cantrell | B64C 3/56 |
| 2018/0074499 | A1 * | 3/2018 | Cantrell | G05D 1/0088 |
| 2018/0074518 | A1 * | 3/2018 | Cantrell | G05D 1/102 |
| 2018/0293444 | A1 * | 10/2018 | Buoro | G06K 9/6289 |
| 2019/0073534 | A1 * | 3/2019 | Dvir | G06V 20/188 |
| 2019/0100311 | A1 * | 4/2019 | Yu | A62C 99/009 |
| 2020/0022312 | A1 * | 1/2020 | Gauvreau, Jr. | A01H 1/027 |

FOREIGN PATENT DOCUMENTS

| | | | |
|---|---|---|---|
| JP | 2017012137 | A | 1/2017 |
| RU | 2588451 | C1 | 6/2016 |
| WO | WO2011090041 | A1 | 7/2011 |
| WO | WO2013099502 | A1 | 7/2013 |

OTHER PUBLICATIONS

Chechetka et al., "Materially engineered artificial pollinators," Chem (2017) 2:224-39.

DeLuca et al. "What's the 'buzz' about? The ecology and evolutionary significance of buzz-pollination," Curr. Op. Plant Biol. (2013) 16(4):429-435.

DeLuca et al., "Variability in bumblebee pollination buzzes affects the quantity of pollen released from flowers," Oecologia (2013) 172:805-16.

DeTar et al., "Acoustically Forced Vibrations of Greenhouse Tomato Blossoms to Induce Pollination," Transactions of ASAE (1968) 731-738.

Gill, "Robotic insect: World's smallest flying robot takes off," BBC News, published online May 2, 2013; available at http://www.bbc.com/news/science-environment-22380287.

Ma et al., "Controlled flight of a biologically inspired, insect-scale robot," Science (2013) 340:603-607.

Ma, "Mechanical design and manufacturing of an insect-scale flapping-wing robot," 2015 Harvard University Ph.D. dissertation; available at https://dash.harvard.edu/bitstream/handle/1/23845433/MA-DISSERTATION-2015.pdf?sequence=1.

Nadis, "What's the buzz? Bees, behavior, and pollination" Harvard University, the Graduate School of Arts and Sciences, published online Aug. 11, 2016; available at https://gsas.harvard.edu/news/stories/what%E2%80%99s-buzz-bees-behavior-and-pollination.

Piore, "Rise of the insect drones," Popular Science, published online Jan. 29, 2014; available at http://www.popsci.com/article/technology/rise-insect-drones.

Shimizu et al., "Development of a non-contact ultrasonic pollination device," Environ. Control Biol. (2015) 53(2): 85-88.

Warsaw University of Technology "B-droid—a robot that's busy as a bee,", published online Feb. 12, 2016; available at https://www.pw.edu.pl/engpw/Research/Business-Innovations-Technology-BIT-of-WUT/B-Droid-a-robot-that-s-busy-as-a-bee.

Wenzke, "This pollinating bee drone shows the power of these endangered creatures," Mashable, published online Feb. 15, 2017, available at http://mashable.com/2017/02/15/bee-drone-project/#kTeoHdqnaqqz.

Wikipedia "Sound pressure," Feb. 22, 2015 [online] ,URL: https://web.archive.org/web/20150222055010/https://en.wikipedia.org/sound_pressure.

* cited by examiner 300
310
Time
302
302
302
304
304
312
312
314
314
314

602
608
608
606
Plant
Plant
608
606
608
606
608
606
Plant
Plant
Plant
604
Field
600

UNMANNED AERIAL VEHICLE FOR AUGMENTING PLANT POLLINATION

CROSS REFERENCE TO RELATED APPLICATIONS

This application is a national stage application under 35 U.S.C. § 371 of International Application No. PCT/US2018/023524, filed internationally on Mar. 21, 2018, which claims priority from U.S. provisional application No. 62,474,534, filed Mar. 21, 2017, entitled "NOVEL METHODS OF AUGMENTING PLANT POLLINATION."

FIELD

This disclosure generally relates to methods of pollinating plants using unmanned aerial vehicles. More specifically, this disclosure relates to inducing plant pollination using a thrust of an unmanned aerial vehicle.

BACKGROUND

Bees play a vital role in plant pollination. Bees induce pollination by beating their wings to vibrate the plant and cause a plant to release pollen; bees are nature's pollination inducers. For a self-pollinating or auto-pollinating plant, this pollen release is sufficient to induce pollination. For a cross-pollinating plant, a bee can transfer the pollen released by a first plant to a second plant by moving between plants.

In recent times, however, bee populations have sharply declined worldwide. The decline in bee populations threatens plant reproduction and also crop yield. Traditional solutions to the bee population problem include manual pollination methods or devices that attach to and vibrate plants.

Manual solutions fail for a variety of reasons. First, manual solutions are labor intensive and time-consuming. Bee populations can number in the hundreds of thousands, with each worker bee inducing pollination in hundreds of plants per day. Manual labor, in contrast, cannot cover the same number of plants without prohibitive costs. Second (and more fundamentally), manual labor cannot consistently replicate bee vibrations.

Device solutions are better, but still severely deficient. Some device solutions include vibrating wires and attachments that physically touch and vibrate a plant in order to induce pollination. Such direct physical contact with a plant increases the risk of injury to the plant. Moreover, these devices are immobile (traditionally mounted on a plant stem) and so cannot pollinate multiple plants or cross-pollinate. Thus, many devices are needed to pollinate the same number of plants as a single bee and none of these devices can cross-pollinate. These devices require significant human labor: each device needs to be placed onto a plant, each device will periodically need a power source change, and each device will need to be removed from a dead plant.

SUMMARY

Examples of the disclosure are directed toward the use of an unmanned aerial vehicle to induce pollination in a plant. The described systems and methods include inducing pollination in a plant by contacting the plant with the thrust generated by a motor of an unmanned aerial vehicle. In some embodiments, a motor of an unmanned aerial vehicle is manipulated so as to change its speed and, thus, produce a thrust with a frequency. The aerial vehicle can pass over or hover over a plant so that its frequency-producing thrust makes contact with the plant and induces the plant to release pollen. For a self-pollinating or auto-pollinating plant, this pollen release is sufficient to result in pollination. For a cross-pollinating plant, this pollen release results in cross-pollination if the pollen is transferred to another plant. As an exemplary advantage, the disclosed methods may obviate the need for traditional pollination methods, such as by bees. Further advantages may include more efficient and cost-effective artificial plant pollination when compared to prior art devices.

An additional exemplary advantage is that autonomous drone pollination precludes the need to physically contact a plant in order to induce pollination of the plant. Other automated systems include wires and clips that physically shake plants in order to induce pollination. As only the thrust of the drone contacts a plant to induce pollen release and pollination, physical contact with, and injury to, a plant is significantly diminished by the described methods. As another exemplary advantage, the disclosed systems and methods may include a navigation system that precludes the need to manually pilot the unmanned aerial vehicle. In contrast to manual pollination methods that are costly and inefficient, automatic navigation and pollination enables large-scale and cost-effective implementation.

In one embodiment, a method of pollinating a plant includes: flying an unmanned aerial vehicle above the plant and generating a thrust that contacts the plant, produces a sound pressure level of at least $6\times10^{-5}$ Pascal (Pa) at the plant, and produces a frequency that induces the plant to release pollen.

In some embodiments, generating a thrust that produces a frequency that induces the plant to release pollen includes changing a speed of a motor of the unmanned aerial vehicle at a frequency that induces the plant to release pollen. In some embodiments, changing the speed of the motor at a frequency that induces the plant to release pollen includes alternating the motor between two speeds.

In some embodiments, generating a thrust that produces a frequency that induces the plant to release pollen includes operating a first motor to produce a first compression wave and operating a second motor to produce a second compression wave that is offset in phase from the first compression wave such that the first and second compression waves combine to produce the thrust at a frequency that induces the plant to release pollen.

In some embodiments, the frequency is between about 200 times per second and about 400 times per second. In some embodiments, the frequency is about 200 times per second to induce an auto-pollinating plant to release pollen. In some embodiments, the frequency is about 400 times per second to induce a cross-pollinating plant to release pollen.

In some embodiments, the method further includes channeling the thrust in the direction of the plant. In some embodiments, the unmanned aerial vehicle further includes multiple variable-pitch propellers.

In some embodiments, the method further includes flying the unmanned aerial vehicle above the plant for a period of time lasting between about 50 milliseconds and about 30 seconds.

In some embodiments, the method further includes automatically navigating the unmanned aerial vehicle along a flight plan. In some embodiments, the flight plan includes locations above two plants.

In some embodiments, the method further includes identifying a type of the plant and determining the flight plan based on the type of the plant. In some embodiments, the method further includes identifying a perimeter of the plant and determining the flight plan based on the perimeter of the plant. In some embodiments, the method further includes identifying a type of the plant and a perimeter of the plant and determining the flight plan based on the type and the perimeter of the plant.

In some embodiments, the method further includes flying the unmanned aerial vehicle above a second plant and generating a second thrust that contacts the second plant, produces a sound pressure level of at least $6\times10^{-5}$ Pa at the second plant, and produces a frequency that induces the second plant to release pollen.

In one embodiment, an unmanned aerial vehicle includes: a propulsion system producing a thrust; and a navigation system controlling the propulsion system and configured to fly the unmanned aerial vehicle above the plant such that the thrust contacts the plant, produces a sound pressure level of at least $6\times10^{-5}$ Pa at the plant, and produces a frequency that induces the plant to release pollen.

In some embodiments, the propulsion system includes a motor, and the navigation system is configured to change a speed of the motor at a frequency that induces the plant to release pollen. In some embodiments, the navigation system is configured to change a speed of the motor at a frequency that induces the plant to release pollen by alternating the motor between two speeds.

In some embodiments, the propulsion system includes a first motor and a second motor, and the navigation system is configured to operate the first motor to produce a first compression wave and operate the second motor to produce a second compression wave offset in phase from the first compression wave such that the first and second compression waves combine to produce the thrust at a frequency that induces the plant to release pollen.

In some embodiments, the frequency is between about 200 times per second and about 400 times per second. In some embodiments, the frequency is about 200 times per second to induce an auto-pollinating plant to release pollen. In some embodiments, the frequency is about 400 times per second to induce a cross-pollinating plant to release pollen.

In some embodiments, the vehicle further includes a thrust channeling mechanism that channels thrust in the direction of the plant. In some embodiments, the vehicle further includes multiple variable-pitch propellers.

In some embodiments, the navigation system is further configured to fly the unmanned aerial vehicle above the plant for a period of time lasting between about 50 milliseconds and about 30 seconds.

In some embodiments, the navigation system is configured to automatically navigate the unmanned aerial vehicle along a flight plan. In some embodiments, the flight plan includes locations above two plants.

In some embodiments, the navigation system includes a computer vision system configured to identify a type of the plant and determine the flight plan based on the type of the plant. In some embodiments, the navigation system includes a computer vision system configured to identify a perimeter of the plant and determine the flight plan based on the perimeter of the plant. In some embodiments, the navigation system includes a computer vision system configured to identify a type of the plant and a perimeter of the plant and determine the flight plan based on the type and the perimeter of the plant.

In some embodiments, the navigation system is configured to fly the vehicle above a second plant such that a thrust of the unmanned aerial vehicle contacts the second plant, produces a sound pressure level of at least $6\times10^{-5}$ Pa at the second plant, and produces a frequency that induces the second plant to release pollen.

DETAILED DESCRIPTION OF EXEMPLARY EMBODIMENTS

In the following description of embodiments, reference is made to the accompanying drawings which form a part hereof, and in which it is shown by way of illustration specific embodiments which can be practiced. It is to be understood that other embodiments can be used and structural changes can be made without departing from the scope of the disclosed embodiments.

Examples of the disclosure are directed toward the use of an unmanned aerial vehicle to induce pollination in a plant. The described systems and methods include inducing pollination in a plant by contacting the plant with the thrust generated by a motor of an unmanned aerial vehicle. In some embodiments, a motor of an unmanned aerial vehicle is manipulated so as to change its speed and, thus, produce a thrust with a frequency. The aerial vehicle can pass over or hover over a plant so that its frequency-producing thrust makes contact with the plant and induces the plant to release pollen. For a self-pollinating or auto-pollinating plant, this pollen release is sufficient to result in pollination. For a cross-pollinating plant, this pollen release results in cross-pollination if the pollen is transferred to another plant. As an exemplary advantage, the disclosed methods may obviate the need for traditional pollination methods, such as by bees. Further advantages may include more efficient and cost-effective artificial plant pollination when compared to prior art devices.

An additional exemplary advantage is that autonomous drone pollination precludes the need to physically contact a plant in order to induce pollination of the plant. Other automated systems include wires and clips that physically shake plants in order to induce pollination. As only the thrust of the drone contacts a plant to induce pollination, physical contact with, and injury to, a plant is significantly diminished by the described methods. As another exemplary advantage, the disclosed systems and methods may include a navigation system that precludes the need to manually pilot the unmanned aerial vehicle. In contrast to manual pollination methods that are costly and inefficient, automatic navigation and pollination enables large-scale and cost-effective implementation.

Figure 1:
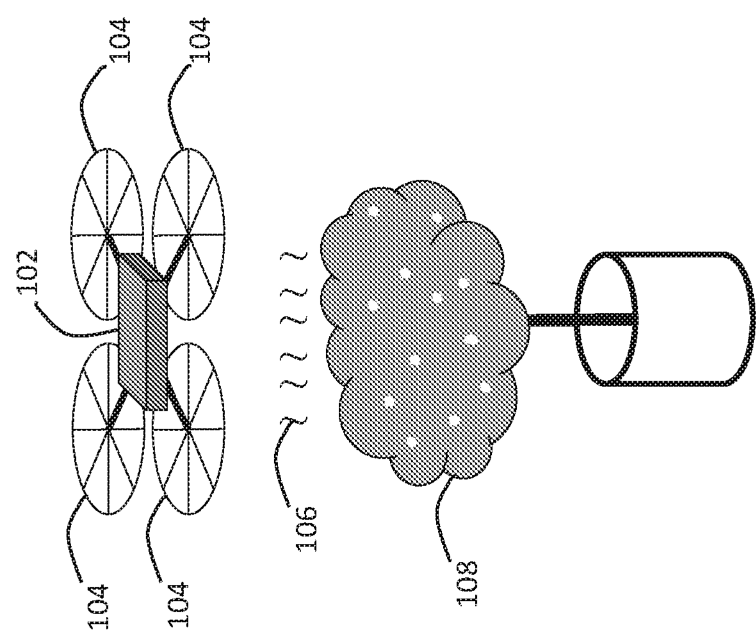
FIG. 1 illustrates an unmanned aerial vehicle pollinating a plant using a thrust, in accordance with an embodiment.

FIG. 1 depicts an unmanned aerial vehicle 102 inducing plant 108 to release pollen. Unmanned aerial vehicle 102 includes propulsion system 104 producing a thrust 106, and a navigation system (not shown) controlling the propulsion system. The navigation system flies unmanned aerial vehicle 102 above plant 108 such that thrust 106 contacts plant 108. Thrust 106 produces a sound pressure level of at least $6\times10^{-5}$ Pa at the plant and produces a frequency that induces plant 108 to release pollen.

In some embodiments, the propulsion system includes a motor, and the navigation system is configured to change a speed of the motor at a frequency that induces plant 108 to release pollen.

In some embodiments, the navigation system is controlled remotely during flight of unmanned aerial vehicle 102 to automatically navigate unmanned aerial vehicle 102 and control thrust 106 of unmanned aerial vehicle 102. In other embodiments, the navigation system is preloaded with instructions to automatically navigate unmanned aerial vehicle 102 and control thrust 106 of unmanned aerial vehicle 102.

Figure 2:
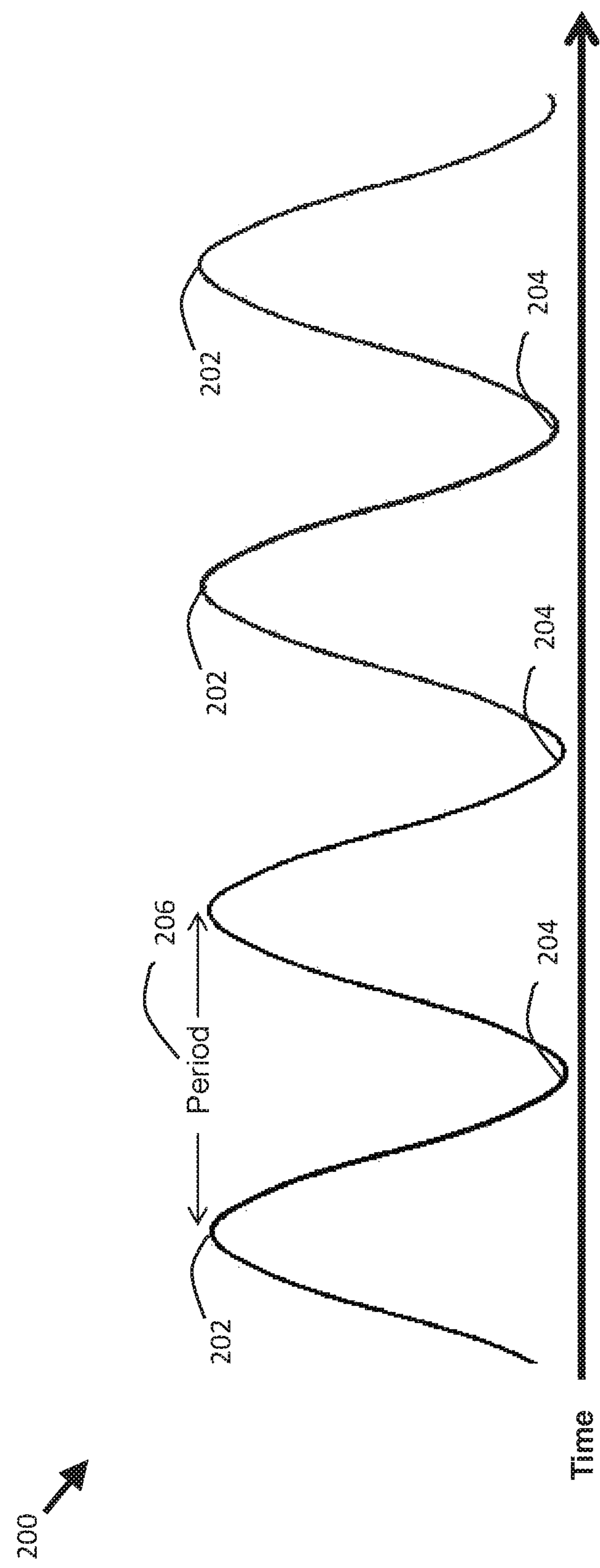
FIG. 2 illustrates a thrust waveform produced by an unmanned aerial vehicle, in accordance with an embodiment.

In some embodiments, the navigation system is configured to change a speed of the motor at a frequency that induces the plant to release pollen by alternating the motor between two speeds. FIG. 2 illustrates a waveform 200 of a motor that changes speed to induce the plant to release pollen. Waveform 200 oscillates between a maximum thrust 202 (corresponding to a high motor speed) and a minimum thrust 204 (corresponding to a low motor speed). The waveform repeats with period 206 creating a thrust frequency that induces the plant to release pollen. In some embodiments, waveform 200 produces is or produces a thrust with a frequency that induces a plant to release pollen.

Figure 3:
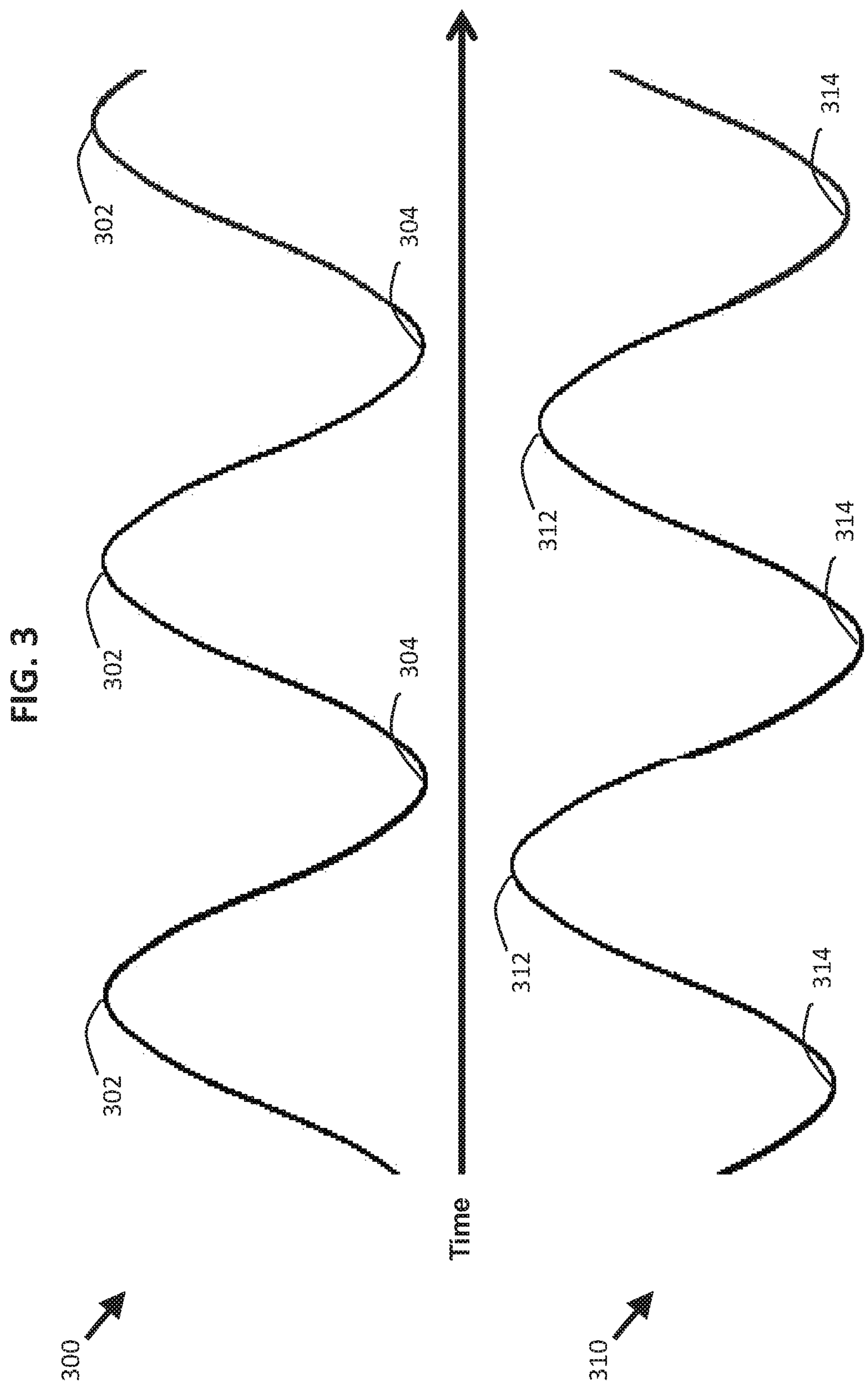
FIG. 3 illustrates a first thrust waveform produced by a first motor of an unmanned aerial vehicle and a second thrust waveform produce by a second motor of the unmanned aerial vehicle, in accordance with an embodiment.

In some embodiments, the propulsion system includes a first motor and a second motor, and the navigation system is configured to operate the first motor to produce a first compression wave and operate the second motor to produce a second compression wave offset in phase from the first compression wave such that the first and second compression waves combine to produce the thrust at a frequency that induces the plant to release pollen. FIG. 3 illustrates waveform 300 of a first motor and waveform 310 of a second motor. Waveform 300 oscillates between a maximum thrust 302 (corresponding to a high motor speed) and a minimum thrust 304 (corresponding to a low motor speed). Waveform 310 oscillates between a maximum thrust 312 (corresponding to a high motor speed) and a minimum thrust 314 (corresponding to a low motor speed). Waveform 300 and waveform 310 may combine to produce the thrust at a frequency that induces the plant to release pollen.

In some embodiments, the frequency is between about 200 times per second and about 400 times per second. This frequency may mimic the frequency at which bees flap their wings. Modulating the speed of a drone at the frequency at which bees flap their wings and thereby pollinate plants allows the drone to artificially augment plant pollination. Compared to plants not pollinated by bees, the described methods may increase pollination by two-thousand percent. The inventor's testing also unexpectedly shows that, compared to plants pollinated by a different thrust frequency, the described apparatuses and methods may increase pollination by over five-hundred percent.

As used herein, a frequency is between about 200 times per second and about 400 times per second if the frequency is approximately 200 times per second, between 200 and 400 times per second, or approximately 400 times per second.

In some embodiments, the frequency is about 200 times per second to induce an auto-pollinating plant to release pollen. In some embodiments, the frequency is about 400 times per second to induce a cross-pollinating plant to release pollen.

In some embodiments, vehicle 102 further includes a thrust channeling mechanism (not shown) that channels thrust in the direction of the plant. In some embodiments, vehicle 102 further includes multiple variable-pitch propellers.

In some embodiments, the navigation system is further configured to fly the unmanned aerial vehicle above the plant for a period of time lasting between about 50 milliseconds and about 30 seconds. As used herein, a period of time lies between the range of about 50 milliseconds to about 30 seconds if the period of time is approximately 50 milliseconds, between 50 milliseconds and 30 seconds, or approximately 30 seconds.

In some embodiments, the navigation system is configured to automatically navigate the unmanned aerial vehicle along a flight plan. In some embodiments, the flight plan includes locations above two plants. In some embodiments, the navigation system is configured to fly the vehicle above a second plant such that a thrust of the unmanned aerial vehicle contacts the second plant, produces a sound pressure level of at least $6\times10^{-5}$ Pa at the second plant, and produces a frequency that induces the second plant to release pollen.

In some embodiments, the navigation system includes a computer vision system configured to identify a type of the plant and determine the flight plan based on the type of the plant. In some embodiments, the navigation system includes a computer vision system configured to identify a perimeter of the plant and determine the flight plan based on the perimeter of the plant. In some embodiments, the navigation system includes a computer vision system configured to identify a type of the plant and a perimeter of the plant and determine the flight plan based on the type and the perimeter of the plant.

Figure 4:
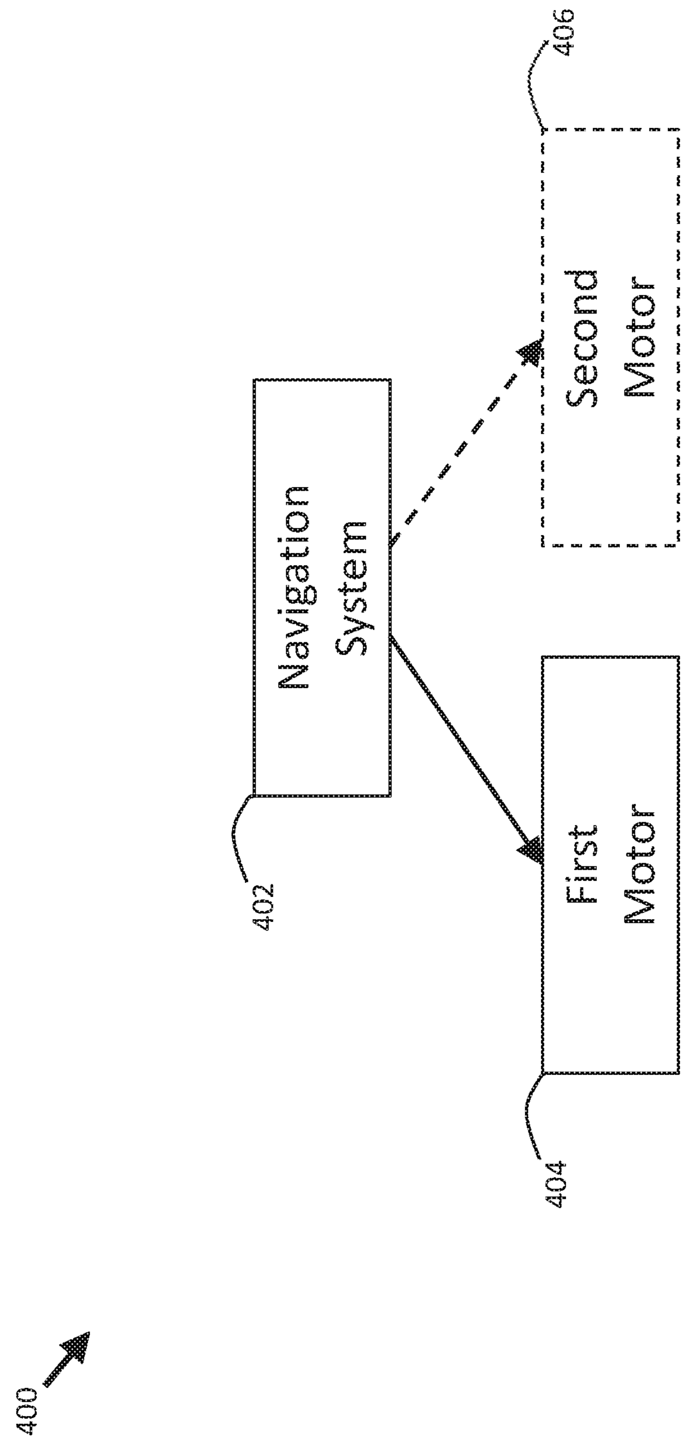
FIG. 4 illustrates an unmanned aerial vehicle, in accordance with an embodiment.

FIG. 4 illustrates unmanned aerial vehicle 400, in accordance with an embodiment. Vehicle 400 includes navigation system 402, first motor 404, and optionally second motor 406. In some embodiments, navigation system 402 includes a computer readable medium (not shown) comprising instructions which, when executed by a computer, cause the computer to carry out the steps of a method. In some embodiments, the method carried out by the computer includes: flying unmanned aerial vehicle 400 above a plant and generating a thrust that contacts the plant, that produces a sound pressure level of at least $6\times10^{-5}$ Pa at the plant, and that produces a frequency that induces the plant to release pollen.

In some embodiments, navigation system 402 is controlled remotely during flight of unmanned aerial vehicle 400 to automatically navigate unmanned aerial vehicle 400 and control the thrust of unmanned aerial vehicle 400. In other embodiments, navigation system 402 is preloaded with instructions to automatically navigate unmanned aerial vehicle 400 and control the thrust of unmanned aerial vehicle 400.

In some embodiments, generating a thrust that produces a frequency that induces the plant to release pollen includes changing a speed of first motor 404 of unmanned aerial vehicle 400 at a frequency that induces the plant to release pollen. In some embodiments, changing the speed of the first motor 404 at a frequency that induces the plant to release pollen includes alternating first motor 404 between two speeds.

In some embodiments, generating a thrust that produces a frequency that induces the plant to release pollen includes operating first motor 404 to produce a first compression wave and operating second motor 406 to produce a second compression wave that is offset in phase from the first compression wave such that the first and second compression waves combine to produce the thrust at a frequency that induces the plant to release pollen.

In some embodiments, the frequency is between about 200 times per second and about 400 times per second. In some embodiments, the frequency is about 200 times per second to induce an auto-pollinating plant to release pollen. In some embodiments, the frequency is about 400 times per second to induce a cross-pollinating plant to release pollen.

In some embodiments, vehicle 400 includes a thrust channeling mechanism. In some embodiments, the unmanned aerial vehicle further includes multiple variable-pitch propellers.

In some embodiments, the method further includes flying unmanned aerial vehicle 400 above the plant for a period of time lasting between about 50 milliseconds and about 30 seconds.

In some embodiments, the method further includes automatically navigating unmanned aerial vehicle 400 along a flight plan. In some embodiments, the flight plan includes locations above two plants.

In some embodiments, the method further includes flying unmanned aerial vehicle 400 above a second plant and generating a second thrust that contacts the second plant, that produces a sound pressure level of at least $6\times10^{-5}$ Pa at the second plant, and that produces a frequency that induces the second plant to release pollen.

Figure 5:
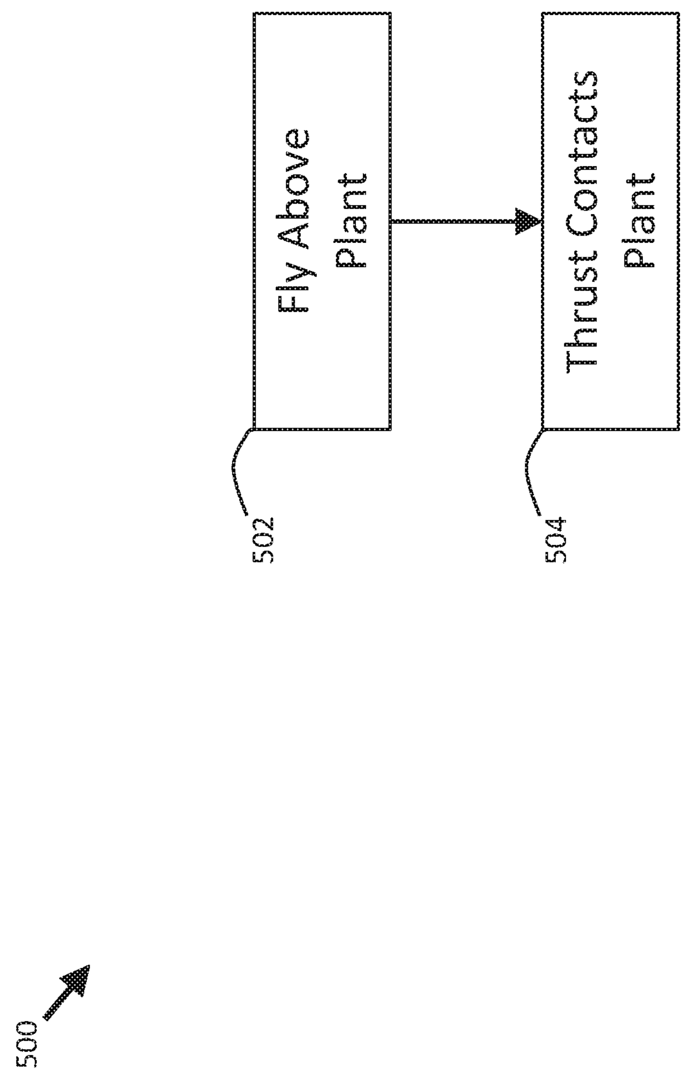
FIG. 5 illustrates a method of pollinating a plant, in accordance with an embodiment.

FIG. 5 illustrates method 500 of pollinating a plant in accordance with an embodiment. Method 500 includes flying an unmanned aerial vehicle above the plant 502 and generating a thrust 504 that contacts the plant, that produces a sound pressure level of at least $6\times10^{-5}$ Pa at the plant, and that produces a frequency that induces the plant to release pollen.

In some embodiments, generating a thrust that produces a frequency that induces the plant to release pollen includes changing a speed of a motor of the unmanned aerial vehicle at a frequency that induces the plant to release pollen.

In some embodiments, changing the speed of the motor at a frequency that induces the plant to release pollen includes alternating the motor between two speeds.

In some embodiments, generating a thrust that produces a frequency that induces the plant to release pollen includes operating a first motor to produce a first compression wave and operating a second motor to produce a second compression wave that is offset in phase from the first compression wave such that the first and second compression waves combine to produce the thrust at a frequency that induces the plant to release pollen.

In some embodiments, the frequency is between about 200 times per second and about 400 times per second. In some embodiments, the frequency is about 200 times per second to induce an auto-pollinating plant to release pollen. In some embodiments, the frequency is about 400 times per second to induce a cross-pollinating plant to release pollen.

In some embodiments, the method further includes channeling the thrust in the direction of the plant. In some embodiments, the unmanned aerial vehicle further includes multiple variable-pitch propellers.

In some embodiments, the method further includes flying the unmanned aerial vehicle above the plant for a period of time lasting between about 50 milliseconds and about 30 seconds.

In some embodiments, the method further includes automatically navigating the unmanned aerial vehicle along a flight plan. In some embodiments, the flight plan includes locations above two plants.

In some embodiments, the method further includes flying the unmanned aerial vehicle above a second plant and generating a thrust that contacts the second plant, that produces a sound pressure level of at least $6\times10^{-5}$ Pa at the second plant, and that produces a frequency that induces the second plant to release pollen.

Figure 6:
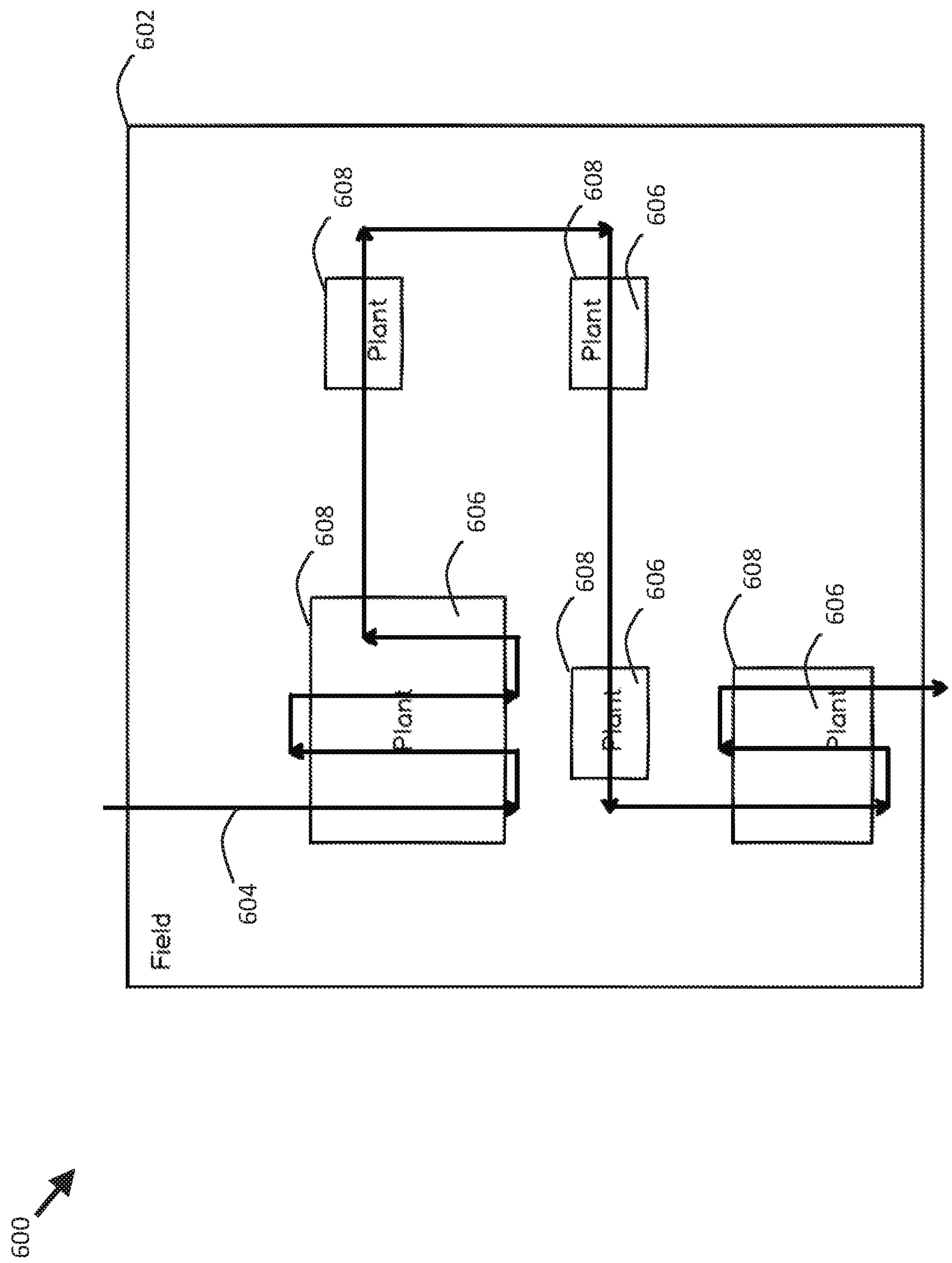
FIG. 6 illustrates a method of using a computer vision system to determine a flight plan that is based on a perimeter of a plant, a type of a plant, or both, in accordance with an embodiment.

FIG. 6 illustrates method 600 of flying an unmanned aerial vehicle on flight plan 604 over field 602 with plants 606, in accordance with an embodiment. The unmanned aerial vehicle includes a navigation system (not shown) configured to navigate the vehicle along flight plan 604. In some embodiments, the navigation system includes a computer vision system (not shown) configured to identify a type of plant 606 and determine the flight plan 604 based on the type. Modifying the flight plan based on the type of plant may advantageously allow for increased pollination of plants; some plants may require more stimulation than others for adequate pollen release and the flight plan can be altered to travel more slowly over those plants or to travel repeatedly over those plants. In some embodiments, the navigation system includes a computer vision system configured to identify a perimeter 608 of the plant and determine the flight plan 604 based on the perimeter 608 of the plant. Modifying the flight plan based on the perimeter of plant may advantageously allow for increased pollination of plants; through identifying the perimeter of the plant, a center of the plant can be approximated and the flight plan can cover the approximate center of the plant. Larger plants can also be accommodated with flight plans that travel repeatedly over such plants. In some embodiments, the computer vision system incorporates a camera and image analyzer configured to identify the type and/or perimeter of the plant. In some embodiments, the computer vision system includes a geographic information system map, such as satellite maps, Google Maps, custom built maps, etc. In some embodiments, the flight path is altered to optimize the amount and/or location of thrust that comes in contact with the plant. In some embodiments, the flight plan may altered by considering any combination of the drone type, the drone size, the plant type, and the plant perimeter.

In some embodiments, identifying a perimeter of a plant may comprise identifying an outer border of the plant or an area of the plant. In some embodiments, the outer border or area is identified by viewing the plant from above. In some embodiments, identifying a perimeter of the plant may comprise differentiating two things (e.g., plant and not plant) and then "boxing" the plant. In some embodiments, the information gathered is combined with latitude and longitude information (e.g., from satellite maps, Google Maps, custom built maps, or in flight determination) to identify the perimeter.

Although the disclosed embodiments have been fully described with reference to the accompanying drawings, it is to be noted that various changes and modifications will become apparent to those skilled in the art. Such changes and modifications are to be understood as being included within the scope of the disclosed embodiments as defined by the appended claims.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

I claim:

1. A method of pollinating a plant, comprising:

flying an unmanned aerial vehicle above the plant; and generating a thrust that contacts the plant that produces a sound pressure level of at least $6\times10^{-5}$ Pascal at the plant and produces a frequency that induces the plant to release pollen, wherein generating the thrust that produces a frequency that induces the plant to release pollen comprises operating a first motor to produce a first compression wave and operating a second motor to produce a second compression wave that is offset in phase from the first compression wave, such that the first and second compression waves combine to produce the thrust at a frequency that induces the plant to release pollen.

2. The method of claim 1, wherein generating the thrust that produces a frequency that induces the plant to release pollen comprises changing a speed of the first motor or the second motor of the unmanned aerial vehicle at a frequency that induces the plant to release pollen.

3. The method of claim 2, wherein changing the speed of the first motor or the second motor at a frequency that induces the plant to release pollen comprises alternating the first motor or the second motor between two speeds.

4. The method of claim 1, wherein the frequency is between about 200 times per second and about 400 times per second.

5. The method of claim 4, wherein the frequency is about 200 times per second to induce an auto-pollinating plant to release pollen.

6. The method of claim 4, wherein the frequency is about 400 times per second to induce a cross-pollinating plant to release pollen.

7. The method of claim 1, further comprising channeling the thrust in the direction of the plant.

8. The method of claim 1, wherein the unmanned aerial vehicle further comprises multiple variable-pitch propellers.

9. The method of claim 1, further comprising flying the unmanned aerial vehicle above the plant for a period of time lasting between about 50 milliseconds and about 30 seconds.

10. The method of claim 1, further comprising automatically navigating the unmanned aerial vehicle along a flight plan.

11. The method of claim 10, wherein the flight plan comprises locations above two plants.

12. The method of claim 1, further comprising identifying a type of the plant and determining the flight plan based on the type of the plant.

13. The method of claim 1, further comprising identifying a perimeter of the plant and determining the flight plan based on the perimeter of the plant.

14. The method of claim 1, further comprising flying the unmanned aerial vehicle above a second plant and generating a second thrust that contacts the second plant, produces a sound pressure level of at least $6\times10^{-5}$ Pascal at the second plant, and produces a frequency that induces the second plant to release pollen.

15. An unmanned aerial vehicle comprising:

a propulsion system comprising a first motor and a second motor, and producing a thrust;

a navigation system controlling the propulsion system and configured to fly the unmanned aerial vehicle above a plant, such that the thrust contacts the plant, produces a sound pressure level of at least $6\times10^{-5}$ Pascal at the plant, and produces a frequency that induces the plant to release pollen, wherein the navigation system is configured to operate the first motor to produce a first compression wave and to operate the second motor to produce a second compression wave offset in phase from the first compression wave, such that the first and second compression waves combine to produce the thrust at a frequency that induces the plant to release pollen.

16. The unmanned aerial vehicle of claim 15, wherein the navigation system is configured to change a speed of the first motor or the second motor at a frequency that induces the plant to release pollen.

17. The unmanned aerial vehicle of claim 16, where the navigation system is configured to change a speed of the first motor or the second motor at a frequency that induces the plant to release pollen by alternating the first motor or the second motor between two speeds.

18. The unmanned aerial vehicle of claim 15, wherein the navigation system is configured to fly the vehicle above a second plant such that a thrust of the unmanned aerial vehicle contacts the second plant, produces a sound pressure level of at least $6\times10^{-5}$ Pascal at the second plant, and produces a frequency that induces the second plant to release pollen.

* * * * *

UNITED STATES PATENT AND TRADEMARK OFFICE

CERTIFICATE OF CORRECTION

PATENT NO. : 11,470,784 B2
APPLICATION NO. : 16/495818
DATED : October 18, 2022
INVENTOR(S) : Gauvreau, Jr.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 608 days.

Signed and Sealed this
Fourteenth Day of January, 2025

Derrick Brent
*Acting Director of the United States Patent and Trademark Office*